United States Patent [19]

Hanifl et al.

[11] Patent Number: 4,779,728
[45] Date of Patent: Oct. 25, 1988

[54] SHARPS DISPOSAL CONTAINER

[75] Inventors: Paul H. Hanifl, Barrington; John J. Newton, Jr., Palatine, both of Ill.; Donald J. Mosior, Lake Geneva, Wis.

[73] Assignee: Sage Products, Inc., Cary, Ill.

[21] Appl. No.: 126,190

[22] Filed: Nov. 27, 1987

Related U.S. Application Data

[63] Continuation-in-part of Ser. No. 934,413, Nov. 24, 1986, Pat. No. 4,715,498.

[51] Int. Cl.⁴ ............................................... B65F 1/16
[52] U.S. Cl. .................................... 206/366; 220/1 T; 206/63.5
[58] Field of Search ................ 206/366, 63.5; 220/1 T

[56] References Cited

U.S. PATENT DOCUMENTS

| | | | |
|---|---|---|---|
| 4,315,592 | 2/1982 | Smith | 206/366 X |
| 4,580,688 | 4/1986 | Harris et al. | 206/366 X |
| 4,674,676 | 6/1987 | Sandel et al. | 206/366 X |
| 4,714,168 | 12/1987 | Johnson et al. | 206/366 X |
| 4,715,498 | 12/1987 | Hanifl | 206/366 |
| 4,722,472 | 2/1988 | Bruno | 206/366 X |

*Primary Examiner*—William Price
*Attorney, Agent, or Firm*—Lee & Smith

[57] ABSTRACT

A disposal container particularly adapted for hospital use and comprising a hollow container body having a slot at the top to permit access to the interior of the container body and having a barrier disposed adjacent the slot for restricting access to the interior of the container body. The barrier comprises a first cowl extending over the slot and a complementary second cowl extending beneath the slot, and a raised shelf at one side of the slot opposite the location of the first cowl. A pivotal closure is provided for sealing of the container when filled.

7 Claims, 2 Drawing Sheets

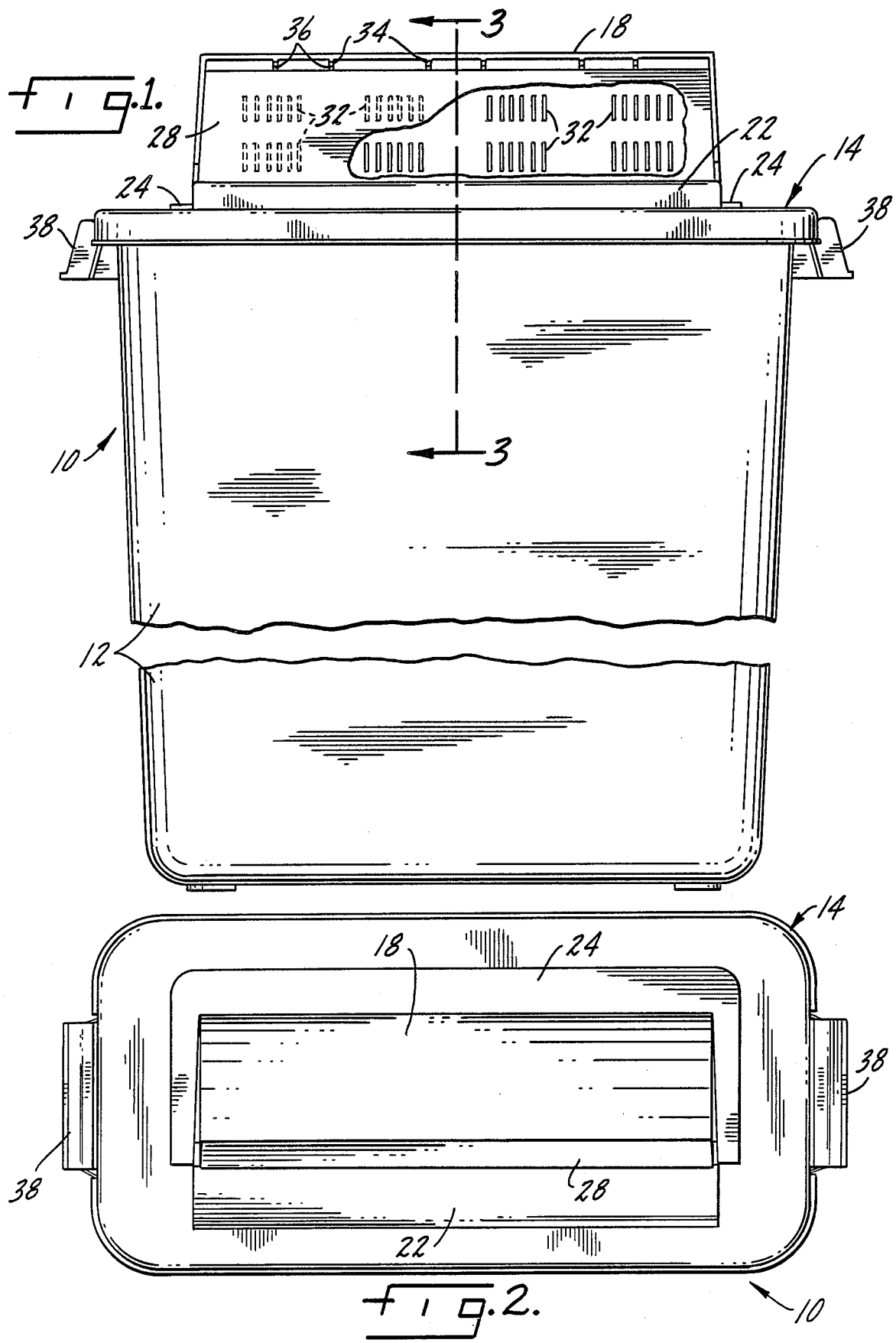

SHARPS DISPOSAL CONTAINER

RELATED APPLICATION

This application is a continuation-in-part of U.S. patent application Ser. No. 934,413 filed Nov. 24, 1986 and now U.S. Pat. No. 4,715,498.

BACKGROUND OF THE INVENTION

This invention relates to disposal of contaminated items, and in particular to a disposal container for use in a hospital or similar environment where contaminated items must be collected and disposed of without creating a hazard for patients or hospital personnel.

In hospitals, clinics and similar medical institutions, contamination is of utmost concern. With the prevention of the spread of communicable diseases being a major priority, disposable, single use patient-care products have become quite prevelant. Those items which can readily transmit disease, such as hypodermic needles and other sharps, are required to be disposed of at their use site under current guidelines of the United States Center For Disease Control. In co-pending U.S. patent application Ser. No. 934,413, filed Nov. 24, 1986, the disclosure of which is incorporated herein by reference, one form of a sharps disposal system is described. The present invention is an improvement over the system of the referenced application, and is directed to a revised form of container which remains secure and yet readily-accessible to the health care practitioner.

SUMMARY OF THE INVENTION

The invention is a disposal container comprising a hollow, upstanding container body having an elongated slot at the top for permitting access to the interior of the container body. A barrier is disposed adjacent the slot for restricting access to the interior of the container body, at least a portion of the barrier comprising a first constriction extending over the slot and a complementary second constriction extending beneath the slot. A closure is provided in the vicinity of the slot for ultimate sealing of the container when filled.

In accordance with the disclosed embodiment of the invention, the barrier includes a raised shelf at one longitudinal side of the slot, and the first constriction comprises a cowl extending from and above the opposite longitudinal side of the slot. The shelf and the cowl define between them a limited opening to the interior of the hollow container body. The second constriction comprises a second cowl extending from the same opposite longitudinal side of the slot beneath the slot in a mirror-image relationship to the first cowl.

The closure is preferably pivotally attached to the disposal container adjacent the slot, and the first cowl is provided with catches for locking the closure to prevent access to the interior of the container body. The catches are formed to engage the closure when the closure is pivoted in one direction past the catches into the interior of the first cowl, the catches being configured to prevent pivoting of the closure in the opposite direction. Preferably, an obstruction is provided at the interface between the first and second cowls to prevent pivoting of the closure into the second cowl.

BRIEF DESCRIPTION OF THE DRAWINGS

The invention is described in greater detail in the following description of an example embodying the best mode of the invention, taken in conjunction with the drawings, in which:

FIG. 1 is a front elevational view, with portions cut away, illustrating the sharps disposal container according to the invention, FIG. 2 is a top plan view thereof.

DESCRIPTION OF AN EXAMPLE EMBODYING THE BEST MODE OF THE INVENTION

Figure 3:
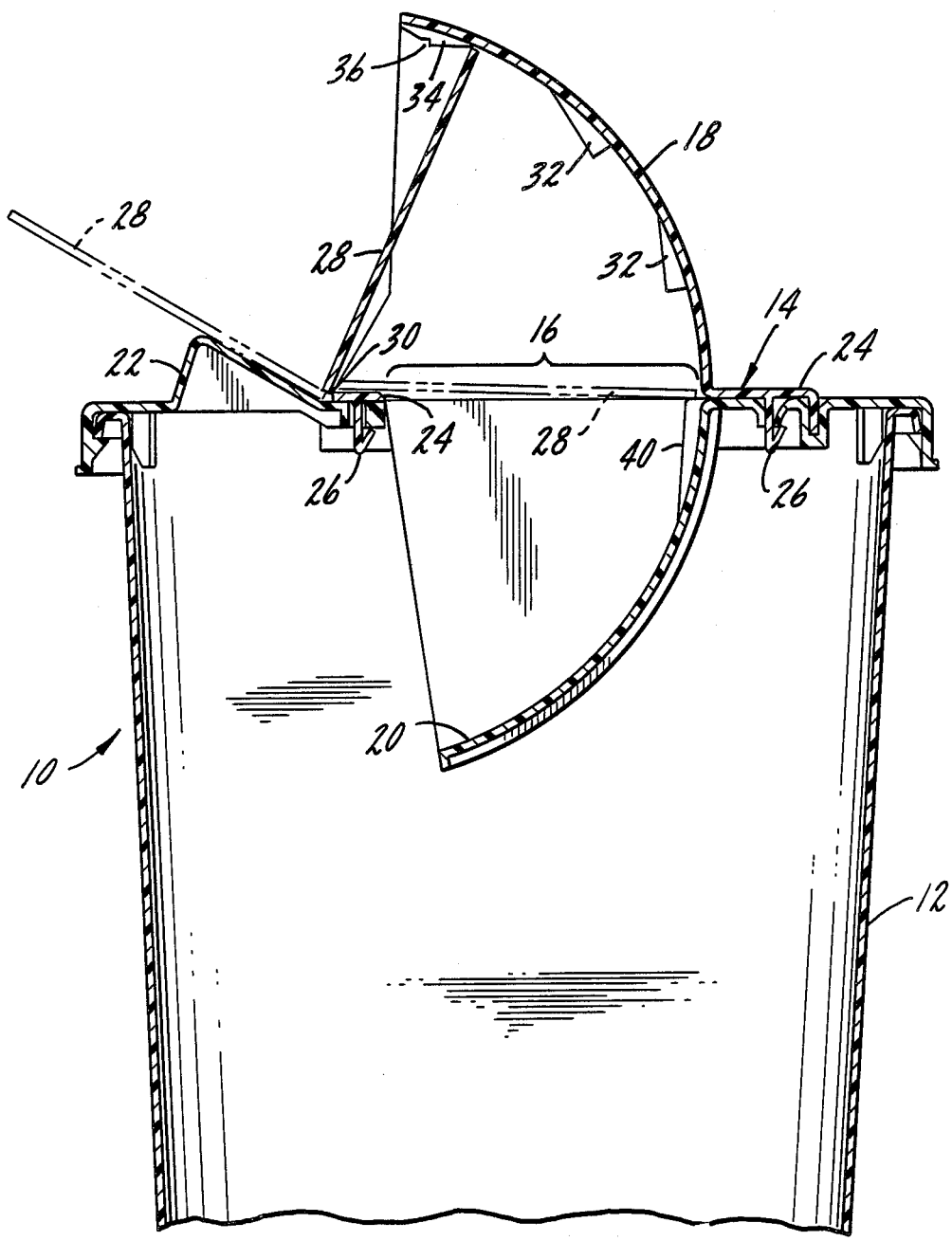
FIG. 3 is an enlarged cross-sectional view taken along lines 3—3 of FIG. 1, with various positions of the closure being shown in phantom.

The sharps disposal container according to the invention is designated generally at 10 in the drawing figures. Primary components of the container 10 are a hollow, upstanding container body 12 and a top 14 formed to be permanently snapped or affixed to the top of the container body 12. The particular means of affixing the top 14 to the container body 12 is unimportant, so long as the two are essentially permanently secured when joined to one another.

The top 14 includes an elongated access slot 16, as shown in FIG. 3. A first constriction is formed over the slot and a complementary second constriction is formed extending beneath the slot, the first constriction comprising a first cowl 18 extending from and above one longitudinal side of the slot 16, and the second constriction comprising a second cowl 20 extending from and beneath the slot 16 in a mirror-image relationship to the first cowl 18.

The first and second cowls 18 and 20 compose part of a barrier disposed at the slot for restricting access to the interior of the container body 12. The remainder of that barrier comprises a raised shelf 22 extending along the opposite side of the slot 16 from which the first cowl 18 is located. The combination of the shelf 22 and cowls 18 and 20 limits access through the slot 16 into the interior of the container body 12 to the extent that it is difficult or impossible for an adult human hand to pass through the slot 16 into the container body 12.

It is preferred that the container body 12 and top 14 be injection molded from an appropriate plastic. In order to permit proper fabrication, the second cowl 20 is formed as an integral portion of the top 14, while the first cowl 18 is a separate element which is snap-locked into appropriate apertures in the top 14. As shown in FIG. 3, the first cowl 18 has a surrounding flange 24 with a series of depending snap elements 26 molded therein for engagement within corresponding apertures in the top 14. Once the cowl 18 is snapped in place, its removal from the remainder of the top 14 is intended to be difficult, if not impossible.

The container 10 is fitted with a pivotal closure 28. The closure 28 is affixed to one portion of the flange 24 adjacent the slot 16 by means of an integral, living hinge 30. During normal use of the container 10, the closure 28 is oriented against the shelf 22, as shown in phantom in FIG. 3. The closure 28 provides a guide into the interior of the container 10 so that used sharps can be readily deposited over the opened closure 28 into the cowl 18 and through the slot 16 into the interior of the container body 12.

When the container 10 has been filled with sharps, it is preferably discarded. In order to secure the contents therewithin, a plurality of catches or locks 32 are formed in the interior of the first cowl 18. By applying pressure to the face of the closure 28, the closure is forced within the first cowl 18 and snaps past the first or both of the catches 32. Due to the configuration of the catches 32, the closure 28 may be pivoted past the catches toward the interior of the container body 12, but is prevented from returning. The contents of the container 10 are therefore secured.

If desired, the first cowl 18 may also include a temporary catch 34 for the closure 28. As shown in FIG. 3, the temporary catch 34 has a notch 36 formed to engage the top edge of the closure 28 to retain the closure in place.

The container 10 is intended to be secured in place during use, such as within a wire rack (not illustrated) on the wall adjacent a patient's bed. When the container is filled, its removal is facilitated by opposite handles 38 on the top 14.

Once the closure 28 has been pivoted within the first cowl 18, it is preferred that the closure 28 be prevented from pivoting past the interface of the first cowl 18 and the second cowl 20. The second cowl 20 is provided with an obstruction 40 which, in combination with that portion of the flange 24 to which the closure 28 is affixed, prevents the closure 28 from being pivoted to greater than essentially the horizontal orientation shown in phantom in FIG. 3 across the slot 16.

While a primary and preferred embodiment of the invention has been illustrated in the drawings and described above, it will evident that various changes can be made to the invention without departing from the spirit thereof or scope of the following claims.

What is claimed is:

1. A disposal container comprising:
 a. a hollow upstanding container body,
 b. an elongated slot at the top of the container body for permitting access to the interior of the container body,
 c. barrier means disposed adjacent said slot for restricting access to the interior of said container body, at least a portion of said barrier means comprising
    i. a first constriction extending over said slot, and
    ii. a complementary second constriction extending beneath said slot, and
 d. a closure disposed adjacent said slot.

2. A disposal container according to claim 1 in which said barrier means includes a raised shelf at one longitudinal side of said slot, and said first constriction comprises a cowl extending from and above the opposite longitudinal side of said slot, said shelf and said cowl defining therebetween a limited opening to said hollow container body.

3. A disposal container according to claim 2 in which said second constriction comprises a second cowl extending from said opposite longitudinal side beneath said slot in mirror-image relationship to said first cowl.

4. A disposal container according to claim 1 in which said first constriction comprises a first cowl extending from and above a longitudinal side of said slot and said second constriction comprises a second cowl extending from and beneath said longitudinal side in mirror-image relationship to said first cowl.

5. A disposal container according to claim 1 in which said closure is pivotal, and said first constriction includes means for locking said closure to prevent access to the interior of said container body.

6. A disposal container according to claim 5 in which said first constriction comprises a cowl extending from and above a longitudinal side of said slot, and said locking means comprises a plurality of catches within said cowl, each catch including stop means engaging said closure when said closure is pivoted in one direction past said stop means into the interior of said cowl, said stop means preventing pivoting of said closure in the opposite direction.

7. A disposal container according to claim 6 including an obstruction preventing pivoting of said closure into said second constriction.

* * * * *